US010064629B2

(12) United States Patent
Macke et al.

(10) Patent No.: US 10,064,629 B2
(45) Date of Patent: Sep. 4, 2018

(54) BONE PERFORATOR (71) Applicant: Zimmer, Inc., Warsaw, IN (US)

(72) Inventors: Jacob Macke, Warsaw, IN (US); Eric Hall, Warsaw, IN (US); Jennifer Molinda, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 361 days.

(21) Appl. No.: 14/738,145

(22) Filed: Jun. 12, 2015

(65) Prior Publication Data

US 2016/0030055 A1 Feb. 4, 2016

Related U.S. Application Data (60) Provisional application No. 62/030,890, filed on Jul. 30, 2014.

(51) Int. Cl.
*A61B 17/00* (2006.01)
*A61B 17/16* (2006.01)

(52) U.S. Cl.
CPC ...... *A61B 17/1604* (2013.01); *A61B 17/1668* (2013.01)

(58) Field of Classification Search
CPC ............ A61B 17/16; A61B 2017/1602; A61B 17/1604; A61B 17/164

USPC ................................ 606/79–85, 86 R, 87–90
See application file for complete search history.

(56) References Cited

U.S. PATENT DOCUMENTS

| 8,657,824 | B2 * | 2/2014 | Sharp .................. | A61B 17/1604 606/80 |
| 2007/0233127 | A1 * | 10/2007 | Tuke .................. | A61B 17/1659 606/79 |
| 2013/0090657 | A1 * | 4/2013 | Bastian .............. | A61B 17/1659 606/79 |

* cited by examiner

*Primary Examiner* — Ellen C Hammond
*Assistant Examiner* — Christina Negrellirodgrigue
(74) *Attorney, Agent, or Firm* — Schwegman Lundberg & Woessner, P.A.

(57) ABSTRACT

A surgeon can place a bone perforator in contact with a bone, and can hammer on the bone perforator. The hammering can drive teeth on the bone perforator into the bone, thereby creating a perforation in the bone. The surgeon can pry or break the bone along the perforation, can access tissue beneath the bone as needed, and can replace the bone along the perforation. In some examples, the bone perforator is formed as a bendable sheet having teeth in a fixed, single-file pattern, with a hammerable surface opposite the teeth. In other examples, the bone perforator has repositionable teeth.

19 Claims, 10 Drawing Sheets

BONE PERFORATOR

CROSS-REFERENCE TO RELATED APPLICATION

This application claims the benefit of U.S. Provisional Application No. 62/030,890, filed Jul. 30, 2014, and incorporated by reference in its entirety herein.

BACKGROUND

In a surgical procedure known as an osteotomy, a surgeon cuts a portion of bone. In some procedures, a surgeon can temporarily remove a portion of bone, access tissue beneath the removed portion, and replace the removed portion. Osteotomies are routinely performed for the hip, knee, jaw, chin, and other suitable parts of the human body. In some examples, a surgeon can perform an osteotomy as a part of a surgical procedure for a human hip. For example, the surgeon can perform an extended trochanteric osteotomy to remove an implanted femoral stem that has failed.

Overview

A surgeon can place a bone perforator in contact with a bone, and can impact the bone perforator, such as with a mallet or hammer (hereinafter referred to as "hammering"). The hammering can drive teeth on the bone perforator into the bone, thereby creating a perforation in the bone. The surgeon can pry or break the bone along the perforation, can access tissue beneath the bone as needed, and can replace the bone along the perforation. Compared with traditional osteotomy procedures that cut or drill the bone, an osteotomy procedure that breaks the bone along a perforation advantageously retains bone material that would otherwise be lost due to the width of a saw blade or a diameter of a drill bit. In some examples, the bone perforator is formed as a bendable sheet having teeth in a fixed, single-file pattern, with a hammerable surface opposite the teeth. In other examples, the bone perforator has repositionable teeth.

This Overview is intended to provide examples of the present patent document. It is not intended to provide an exclusive or exhaustive explanation of the invention. The Detailed Description below is included to provide further information about the present bone perforator and method for perforating bone.

BRIEF DESCRIPTION OF THE DRAWINGS

In the drawings, which are not necessarily drawn to scale, like numerals describe similar components in different views. The drawings illustrate generally, by way of example, but not by way of limitation, various embodiments discussed in the present patent document.

DETAILED DESCRIPTION

A surgeon can use a bone perforator to form a perforation in a bone. The surgeon can perforate the bone, pry or break the bone along the perforation, access tissue or one or more other structures beneath the bone as needed, and can replace the bone along the perforation.

As a specific example, for some patients that have had hip replacement surgery, the implanted femoral stem may become damaged or infected. To treat the damage or infection, a surgeon can surgically remove the implanted femoral stem. Femoral stems often extend downward to a significant depth from a top end of the femur. In order to access the full extent of the femoral stem, a surgeon can perforate the femur along a perforation, pry or break the femur along the perforation to form a broken region within the perforation, remove or fold over the broken region to access the implanted femoral stem, and replace the broken region once the implanted femoral stem has been removed or replaced. After surgery, the femur can heal with the broken region in its original position. Perforating and breaking the femur, rather than cutting, sawing or drilling, can reduce or minimize the amount of bone lost during the procedure, which is desirable.

Figure 1:
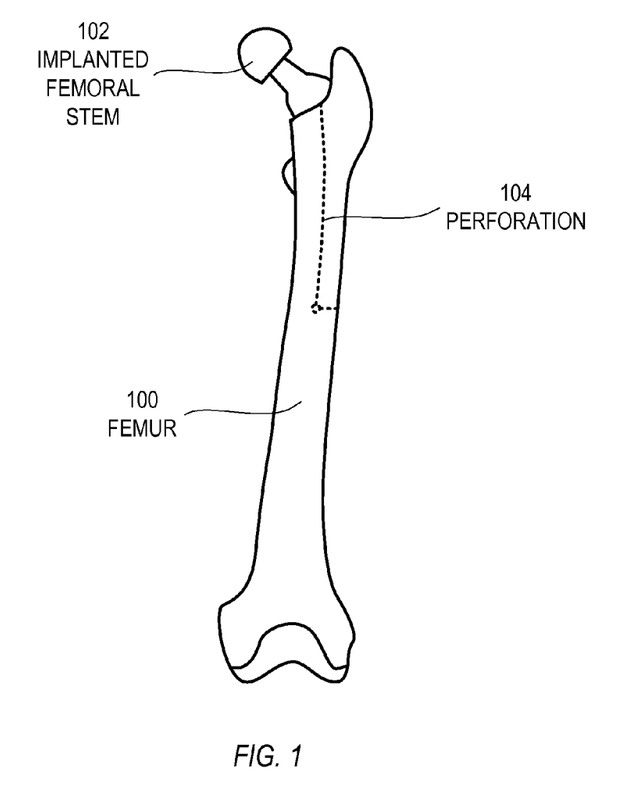
FIG. 1 shows a side view of an example of a perforation formed in a femur.

FIG. 1 shows a side view of an example of a perforation 104 formed in a femur 100. Such a perforation 104 can provide access to an implanted femoral stem 102. In some examples, such as the example of FIG. 1, the perforation 104 can extend partially around a portion at the proximal or top edge of the femur 100. In other examples, the perforation can form a closed path, and can extend fully around a portion of the femur 100 away from the top edge of the femur 100. The example of FIG. 1 is but one example; other suitable perforation shapes can be used. Other suitable surgical procedures can also perforate a portion of bone, then pry or break the bone along the perforation, rather than cut the bone with a saw or drill the bone with a drill bit.

Figure 2:
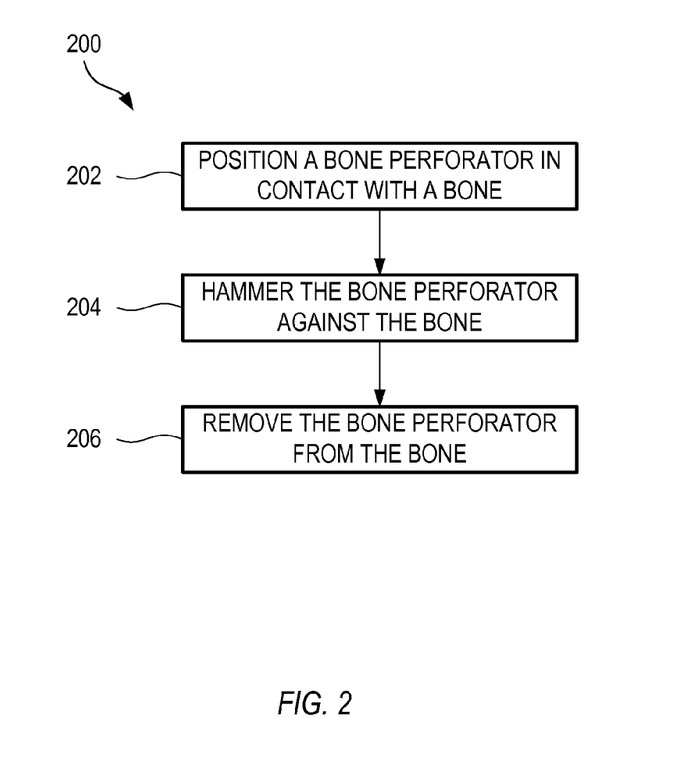
FIG. 2 is a flow chart of an example of a method for perforating bone.

FIG. 2 is a flow chart of an example of a method 200 for perforating bone. The method 200 can be used to produce the perforation 104 of FIG. 1; other suitable methods can also be used.

At 202, method 200 positions a bone perforator in contact with a bone. The bone perforator can include teeth that extend toward the bone and define a perforating path. At 204, method 200 hammers the bone perforator, on a side of the bone perforator opposite the teeth, against the bone, so that the teeth pierce the bone along the perforating path and areas between the teeth do not pierce the bone. The hammering produces a perforation in the bone in the shape of the perforating path. At 206, method 200 removes the bone perforator from the bone.

In some examples, the perforating path on the bone perforator is a closed path. For these examples, a portion of the bone within the closed path forms a removable portion. In some of these examples, method 200 can further pry the removable portion away along the closed path to fold over or remove the removable portion. In some of these examples, method 200 can further replace the removable portion in its original location.

In other examples, the perforating path on the bone perforator is not a closed path. For these examples, method 200 can further include alternately repositioning the bone perforator against the bone to extend the perforating path, and hammering the bone perforator, on a side opposite the teeth, against the bone, so that the teeth pierce the bone along the extended perforating path and areas between the teeth do not pierce the bone. The method 200 can repeat the repositioning and hammering until the extended perforating path forms a closed path on the bone. A portion of the bone within the closed path can form the removable portion. In some of these examples, method 200 can further pry the removable portion away along the closed path to fold over or remove the removable portion. In some of these examples, method 200 can replace the removable portion in its original location.

Figure 3:
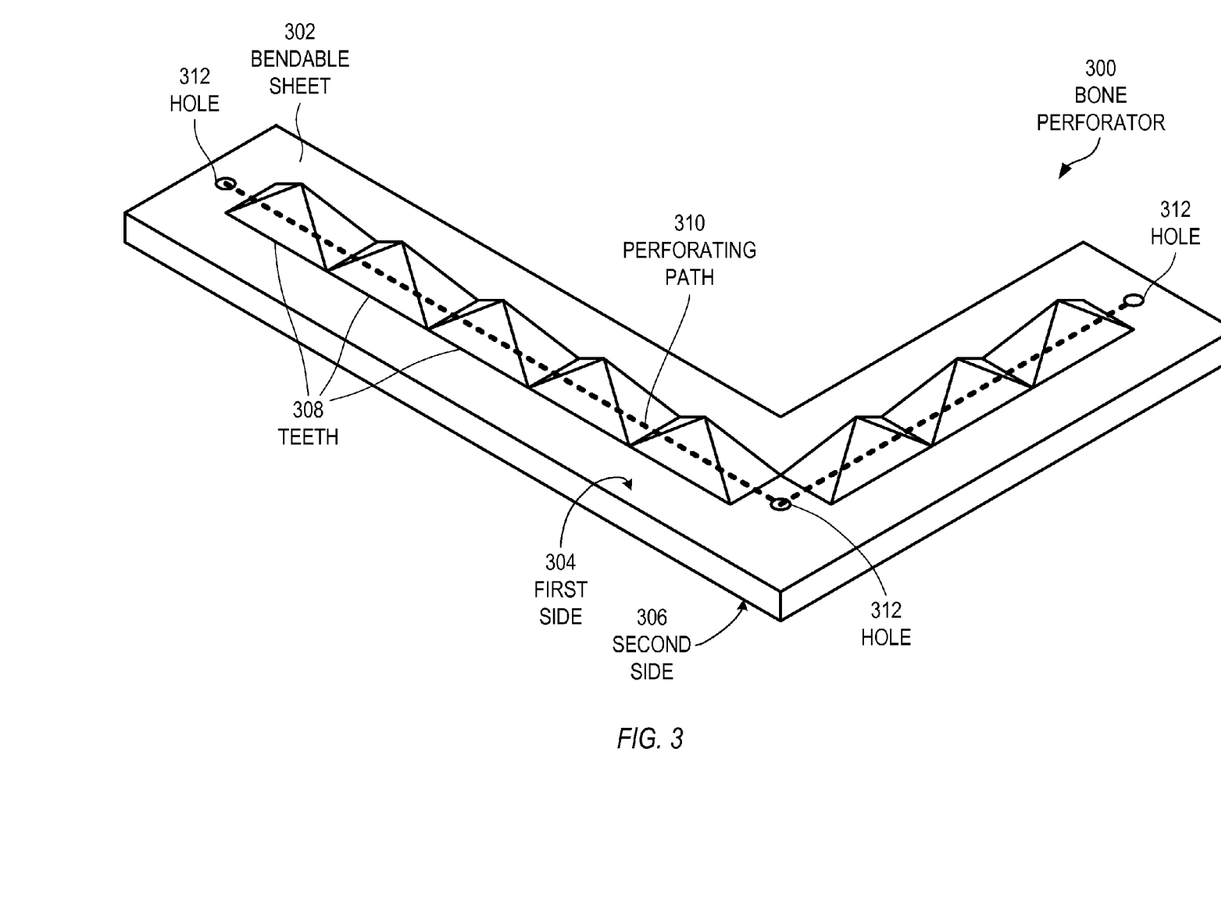
FIG. 3 is a perspective view of an example of a bone perforator having teeth that are in a fixed position with respect to one another (e.g., are non-repositionable).

FIG. 3 is a perspective view of an example of a bone perforator 300 having teeth 308 that are in a fixed position with respect to one another (e.g., are non-repositionable). In some examples, the bone perforator 300 can be used to execute the method 200 of FIG. 2, and can produce the perforation 104 of FIG. 1. The bone perforator 300 is but one example; other suitable bone perforators can also be used.

The bone perforator 300 can be formed as a bendable sheet 302 having opposing first and second sides 304, 306. In some examples, the sheet 302 can be configured to be bent cylindrically around a bone, such as an exterior of a femur. The sheet 302 can be formed from rubber, plastic, cloth, or another suitable bendable material.

The bone perforator 300 can include a plurality of teeth 308 extending from the first side 304 of the sheet 302. The teeth 308 can be spaced along a single-file perforating path 310. The second side 306 of the sheet 302 can be a hammerable surface, so that when the second side 306 of the sheet 302 is hammered against a bone, the plurality of teeth 308 form a perforation in the bone in the shape of the perforating path 310.

In some examples, the second side 306 of the sheet 302 is flat. In some examples, away from the perforating path 310, the sheet 302 can have a constant thickness between the first and second sides 304, 306. In other examples, proximate the perforating path 310, the sheet 302 can be thicker than at regions away from the perforating path 310.

In the example of FIG. 3, the perforating path 310 is L-shaped. Such an L-shaped perforating path 310 can be used to form two adjacent segments of a rectangular perforation. For instance, one leg of the L-shape can form a generally flat perforation segment parallel to an axis of a generally cylindrical bone, while the other leg of the L-shape can form a circumferential perforation segment around the cylindrical bone. The bone perforator 300 of FIG. 3 can be used to form the two adjacent segments of the rectangular perforation, then can be removed and repositioned on the bone to form the other two adjacent segments of the rectangular perforation. The L-shape is but one example for the perforating path 310; other suitable perforating path shapes can also be used.

In some examples, the sheet 302 defines at least one hole 312 from the first side 304 to the second side 306. A surgeon can use a hook, a suture, or another suitable instrument to engage one or more of the holes 312, and pull the bone perforator 300 away from the perforated bone after the perforation has been formed. In some examples, each hole 312 extends across opposite sides of the perforating path 310. Locating the holes 312 along or near the perforating path 310 can reduce or eliminate torques that arise during removal of the bone perforator 300 from the bone, which can be beneficial. In some examples, holes 312 are located at longitudinal ends of the perforating path 310. In some examples, the holes 312 are positioned in pairs, with one pair being positioned at a first longitudinal end of the perforating path 310, and a second pair being positioned at a second longitudinal end of the perforating path 310, opposite the first longitudinal end. Each pair of holes can function as a suture anchor, so that a surgeon can thread a suture through the pair of holes, and can pull on the suture to help reposition the bone perforator 300 or remove the bone perforator 300 after use.

In some examples, the teeth 308 in the plurality are rigid. These rigid teeth 308 can be formed from a material different from that of the sheet 302, and can be attached to the sheet 302. The teeth 308 can be spaced evenly along the perforating path 310, or can be spaced unevenly along the perforating path 310. In the example of FIG. 3, the teeth 308 are shaped as pyramids, with each side of the pyramid being flat, and the pyramid sides converging at a point farthest away from the first side 304 of the sheet 302. The teeth can also have other suitable shapes, such as cones. In some examples, such as the examples of FIGS. 4 and 5, the teeth can converge to a ridge.

Figure 4:
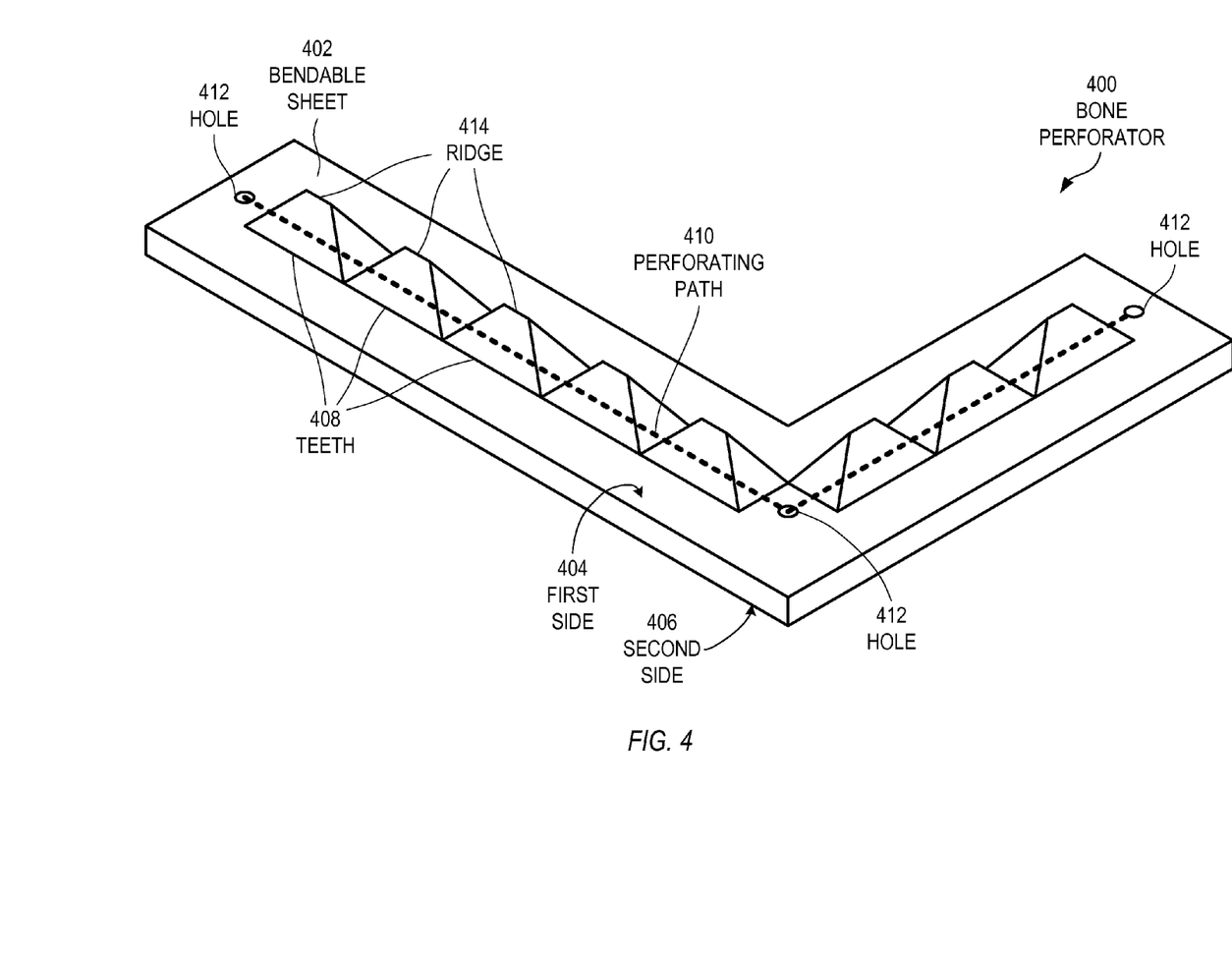
FIG. 4 is a perspective view of another example of a bone perforator having teeth that are in a fixed position with respect to one another.

FIG. 4 is a perspective view of another example of a bone perforator 400 having teeth 408 that are in a fixed position with respect to one another (e.g., are non-repositionable). The bone perforator 400 can be used to execute the method 200 of FIG. 2, and can produce the perforation 104 of FIG. 1. The bone perforator 400 is but one example; other suitable bone perforators can also be used.

The bone perforator 400 can also be formed as a bendable sheet 402 having opposing first and second sides 404, 406, and can include a plurality of teeth 408 extending from the first side 404 of the sheet 402 and spaced along a single-file perforating path 410. The bendable sheet 402 can also define at least one hole 412 from the first side 404 to the second side 406.

Whereas the bone perforator 300 of FIG. 3 included pyramidal teeth, the teeth 408 in FIG. 4 can extend away from the first side 404 to a ridge 414. The ridge 414 can be elongated in a direction parallel to the perforating path 410 at the respective tooth 408. The ridges 414, aligned with the perforating path 410, can be beneficial in forming a perforation in the bone. In some examples, each ridge 414 can have a longitudinal length equal to the space between adjacent ridges 414. In any of these examples, individual teeth can have any suitable shape.

Figure 5:
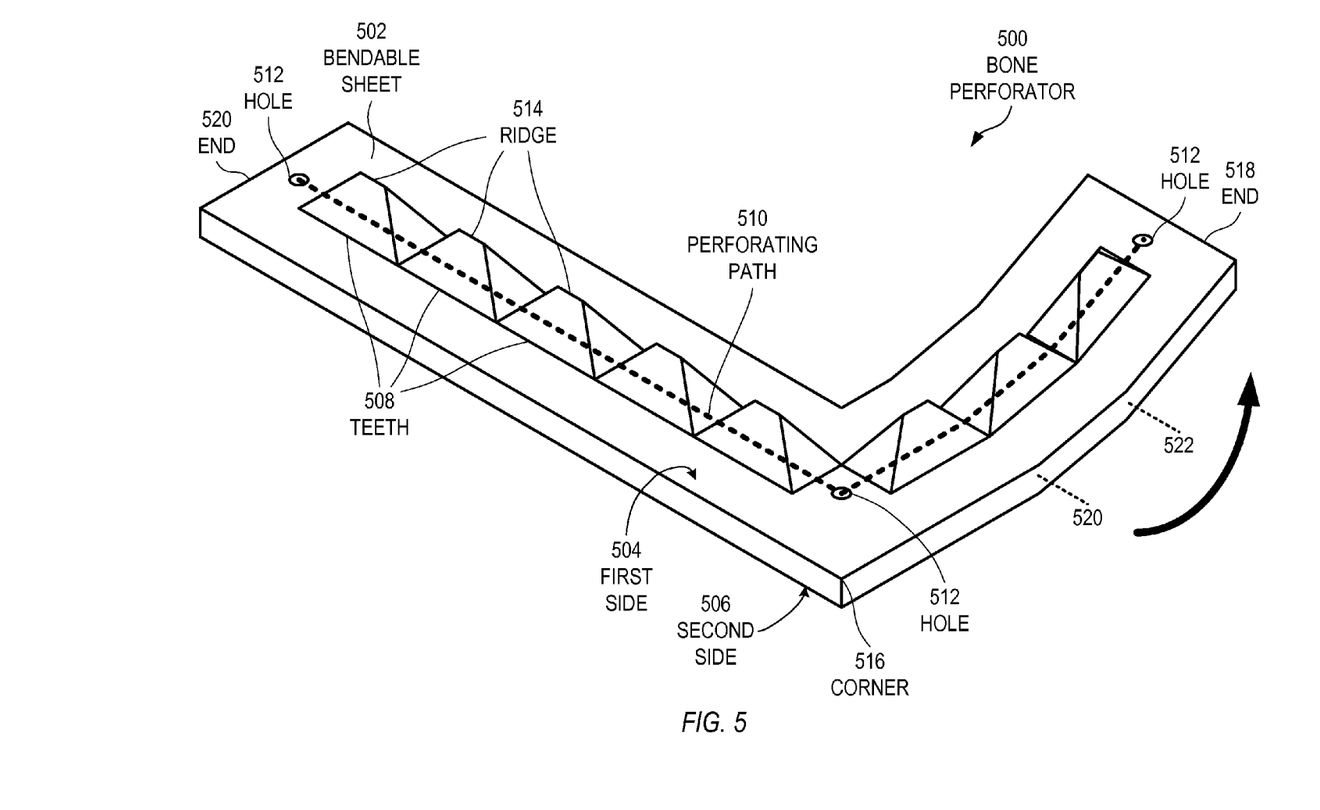
FIG. 5 is a perspective view of an example of the bone perforator of FIG. 4, partially bent to wrap circumferentially around a bone.

FIG. 5 is a perspective view of an example of the bone perforator 400 of FIG. 4, partially bent to wrap circumferentially around a bone. Elements numbered 5xx of FIG. 5, between 500 and 514, are identical in structure and function to elements numbered 4xx of FIG. 4.

In the example of FIG. 5, the bendable sheet 502 is bent along a segment extending from corner 516 to end 518. In this example, the bending occurs at axes 520, 522, although the sheet 502 can also bend at other locations. In the example of FIG. 5, the bendable sheet 502 remains flat between corner 516 and end 520.

Figure 6:
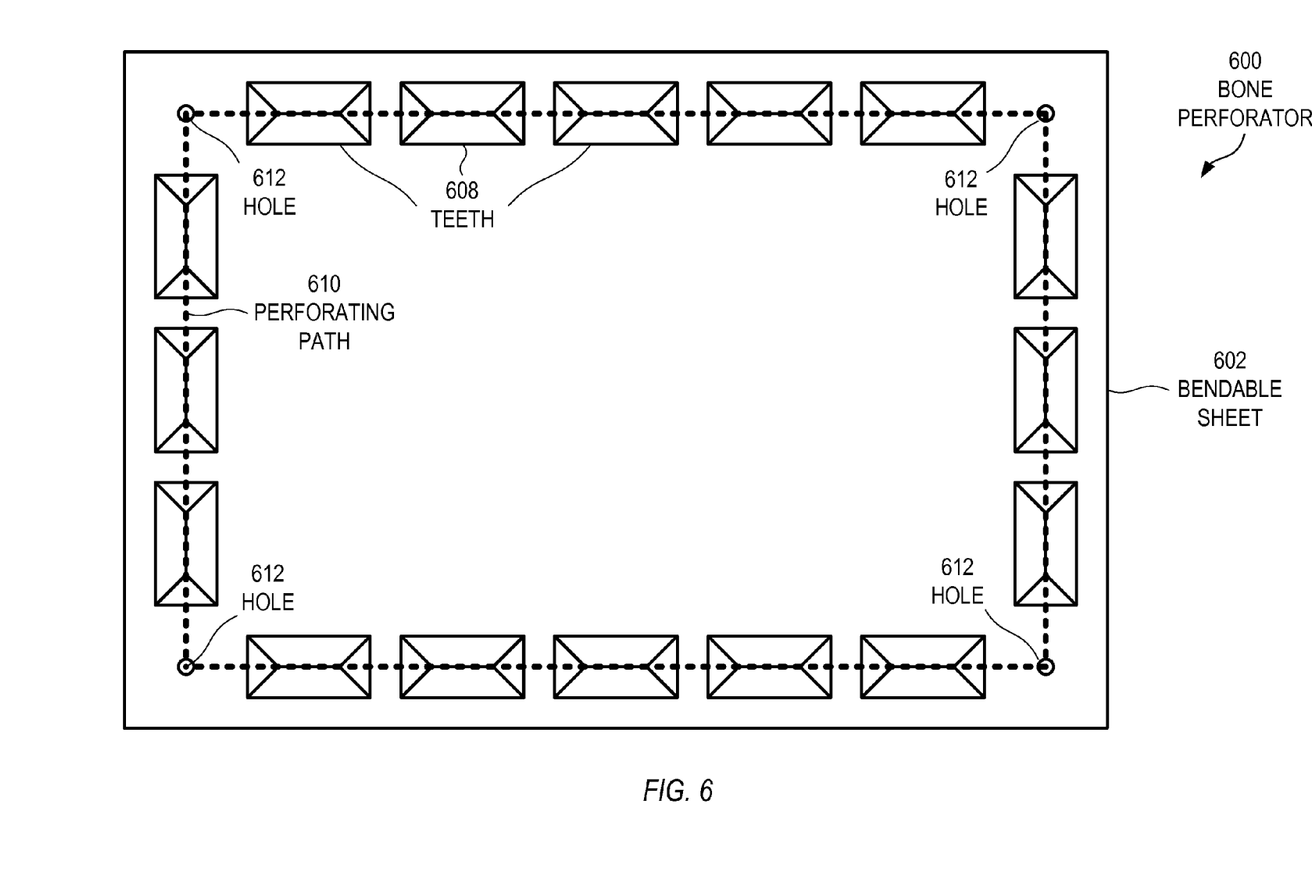
FIG. 6 shows an example of a first side of a bone perforator having teeth that are in a fixed position with respect to one another.

FIG. 6 shows an example of a first side of a bone perforator 600 having teeth 608 that are in a fixed position with respect to one another (e.g., are non-repositionable).

The bone perforator 600 can be used to execute the method 200 of FIG. 2, and can produce the perforation 104 of FIG. 1. The bone perforator 600 is but one example; other suitable bone perforators can also be used.

Whereas the perforating paths 310, 410, 510 of FIGS. 3-5 are open-ended (e.g., the paths extend from one longitudinal end to another longitudinal end), the teeth 608 in the example of FIG. 6 are spaced along a closed perforating path 610. In the example of FIG. 6, the sheet 602 defines holes 612 therethrough at corners of the perforating path 610; however, other locations can also be used.

In the example of FIG. 6, the teeth 608 have bases that are spaced apart from one another, compared with bases that are directly adjacent to one another, as in FIGS. 3-5. In any of the examples of FIGS. 3-6, some or all of the teeth can have bases that are spaced apart, and some or all of the teeth can have bases that are directly adjacent to other bases.

The examples shown in FIGS. 3-6 include non-repositionable teeth (e.g., teeth that are in a fixed position with respect to one another, even as the bendable sheet is bent). In some of these examples, the teeth are arranged in a straight line or in a concatenated series of straight lines. In other examples, the teeth can be repositioned as needed, so that a surgeon can form a perforation along an arbitrary desired path on a bone.

Figure 7:
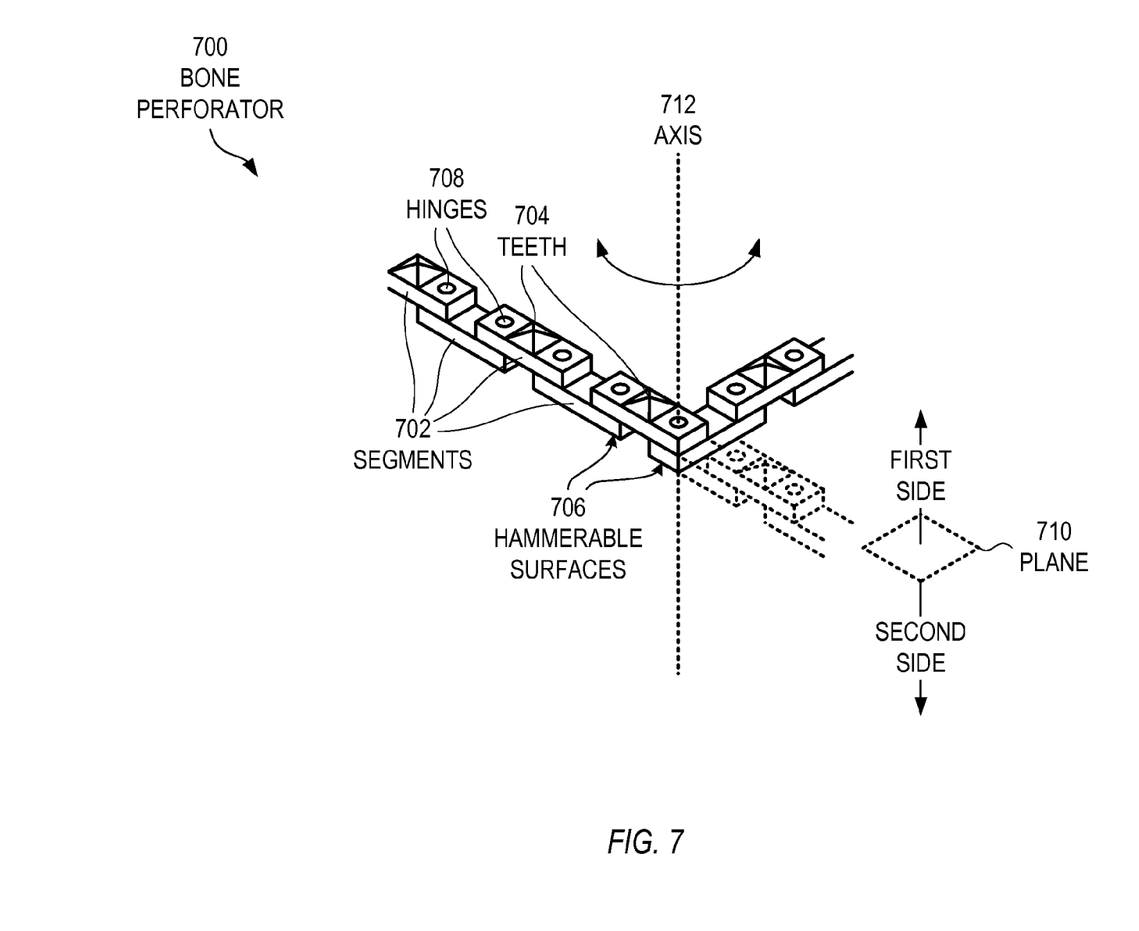
FIG. 7 is a perspective view of an example of a bone perforator having teeth that are repositionable with respect to one another.

FIG. 7 is a perspective view of an example of a bone perforator 700 having teeth 704 that are repositionable with respect to one another. The bone perforator 700 can be used to execute the method 200 of FIG. 2, and can produce the perforation 104 of FIG. 1. The bone perforator 700 is but one example; other suitable bone perforators can also be used.

The bone perforator 700 includes a plurality of segments 702 hinged sequentially to one another along a single-file perforating path. At least some of the segments 702 in the plurality include teeth 704 extending away from the segments 702. At least some of the segments 702 in the plurality include a hammerable surface 706, so that when the hammerable surfaces 706 of the segments 702 are hammered against a bone, the plurality of teeth 704 form a perforation in the bone in the shape of the perforating path.

In the example of FIG. 7, hinges 708 can connect adjacent segments to each other in a manner similar to that of a typical bicycle chain. Each hinge can include a post (not shown in FIG. 7) that extends between a pair of adjacent segments, so that the segments in the pair can pivot around the post, with respect to each other. In some examples, the bone perforator 700 can include hinges 708 that are parallel to one another and oriented so that the perforating path is repositionable within a plane, such as plane 710. In the example of FIG. 7, the posts extend perpendicular to the plane 710, parallel to axis 712. In some examples, at least some of the segments 702 in the plurality can include teeth 704 extending away from the plane 710 on a first side of the plane 710. In some examples, the hammerable surface 706 can be disposed on a second side, opposite the first side of the plane 710.

In some examples, the segments 702 can all be rigid. For these examples, the teeth 704 can be repositioned within plane 710, but not outside of plane 710. In other examples, at least some of the segments 702 can be bendable, so that bending at least one of the segments bends the perforating path out of the plane.

Figure 8:
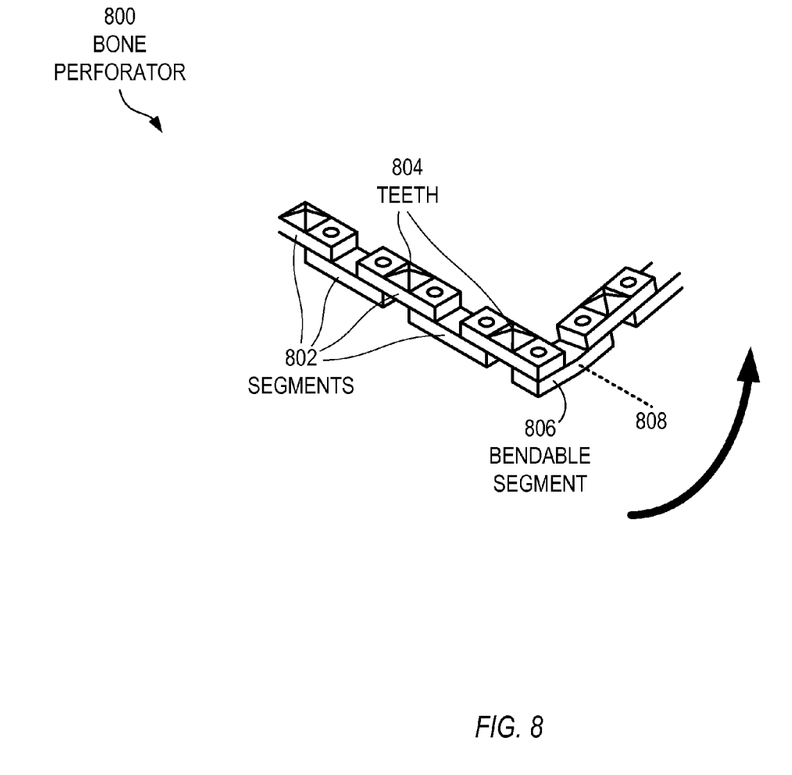
FIG. 8 is a perspective view of an example of a bone perforator having teeth that are repositionable with respect to one another, and having at least one bendable segment.

For instance, FIG. 8 is a perspective view of an example of a bone perforator 800 having teeth 804 that are repositionable with respect to one another, and having at least one bendable segment 806. In the example of FIG. 8, bendable segment 806 is bent along axis 808.

Figure 9:
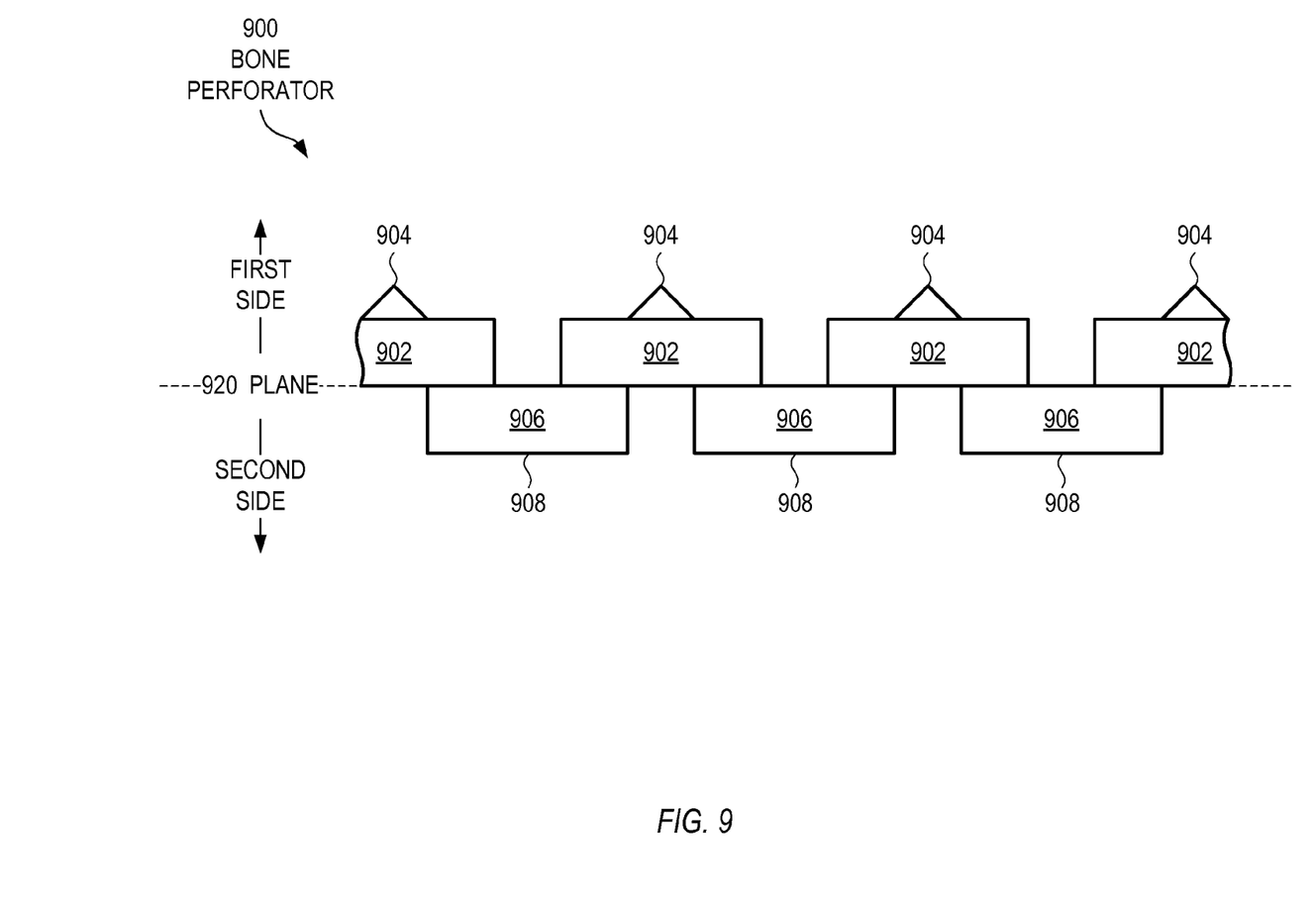
FIG. 9 shows a side view of an example of a bone perforator.

FIG. 9 shows a side view of an example of a bone perforator 900. In this example, bone perforator 900 includes upper segments 902 disposed on a first side of plane 920. The upper segments 902 include the teeth 904. In this example, the bone perforator 900 also includes lower segments 906 disposed on a second side of the plane 920, opposite the first side. The lower segments 906 include the hammerable surfaces 908. In some of these examples, at least some of the upper segments 902 can be rigid, and at least some of the lower segments 906 can be bendable. In other examples, at least some of the upper segments 902 can be bendable, and at least some of the lower segments 906 can be rigid. In some examples, the upper segments 902 are all rigid. In other examples, the upper segments 902 are all bendable. In some examples, the lower segments 906 are all rigid. In some examples, the lower segments 906 are all bendable.

Figure 10:
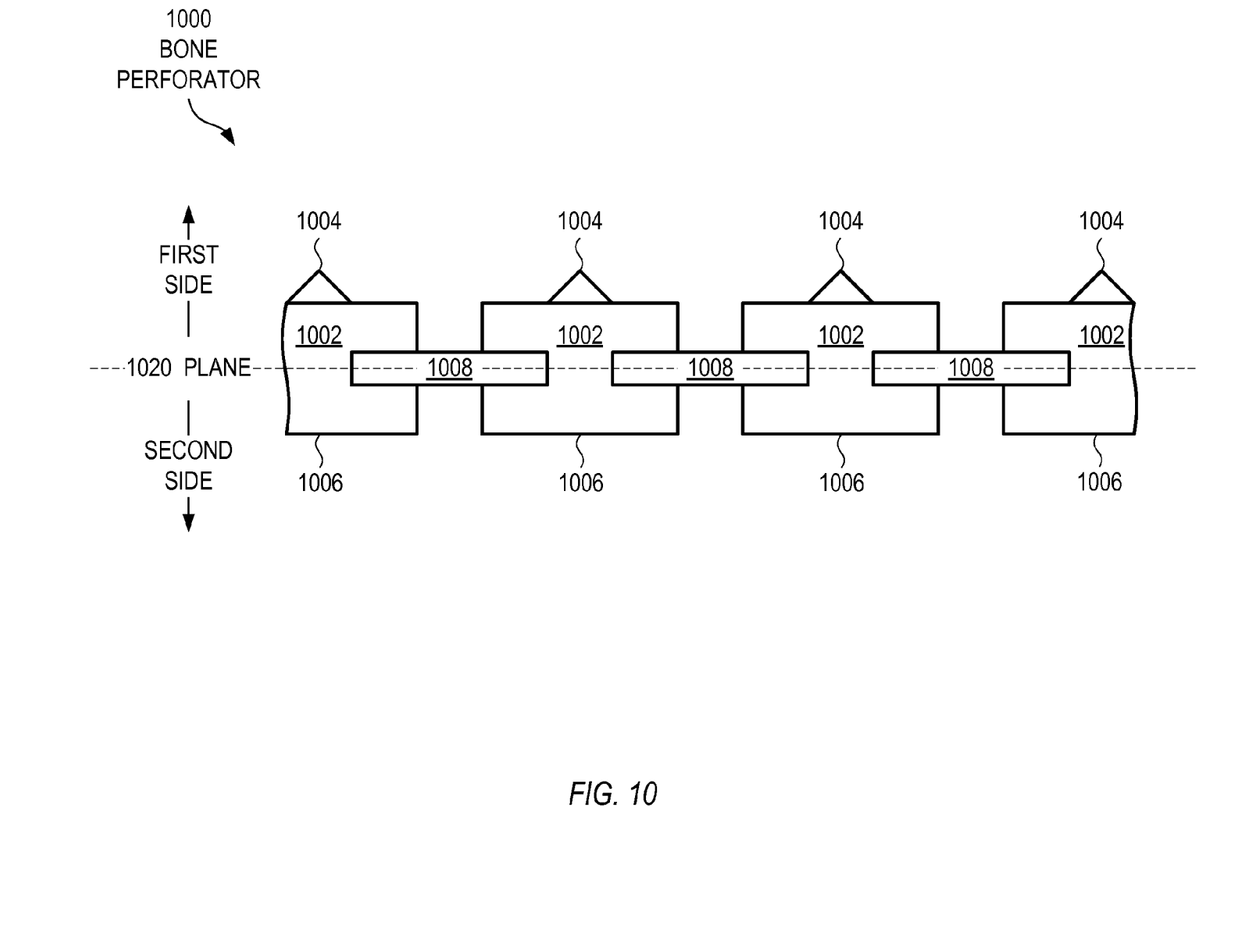
FIG. 10 shows a side view of another example of a bone perforator.

FIG. 10 shows a side view of another example of a bone perforator 1000. In this example, bone perforator 1000 can include mounting segments 1002. Each mounting segment 1002 can straddle plane 1020. The mounting segments 1002 can include teeth 1004 disposed on a first side of the plane 1020, and hammerable surfaces 1006 disposed on a second side of the plane 1020, opposite the first side. In this example, bone perforator 1000 can include connecting segments 1008 between the mounting segments 1002, and hingedly connected to adjacent mounting segments 1002. Some or all of the mounting segments 1002 can be bendable. Some or all of the connecting segments 1008 can be bendable.

FIGS. 9 and 10 are but two examples of constructions for bone perforators having repositionable teeth. These constructions can be mixed and matched as needed. Other suitable constructions can also be used. Other types of hinges can also be used, including barrel hinges, pivot hinges, butt/mortise hinges, case hinges, ball-and-socket hinges, and others.

The following non-limiting list of examples can further illustrate the present bone perforator and method for perforating bone.

In Example 1, a method for perforating bone can comprise positioning a bone perforator in contact with a bone, the bone perforator including teeth that extend toward the bone and define a perforating path; hammering the bone perforator, on a side of the bone perforator opposite the teeth, against the bone, so that the teeth pierce the bone along the perforating path and areas between the teeth do not pierce the bone; and removing the bone perforator from the bone.

In Example 2, the method of Example 1 can optionally be configured such that the perforating path is a closed path; and a portion of the bone within the closed path forms a removable portion.

In Example 3, the method of Examples 1 or 2 can optionally further comprise prying the removable portion away along the closed path to fold over or remove the removable portion.

In Example 4, the method of Example 3 can optionally further comprise replacing the removable portion in its original location.

In Example 5, the method of one of Examples 1-4 can optionally further comprise alternately: repositioning the bone perforator against the bone to extend the perforating path; and hammering the bone perforator, on a side opposite the teeth, against the bone, so that the teeth pierce the bone along the extended perforating path and areas between the teeth do not pierce the bone, until the extended perforating path forms a closed path on the bone; wherein a portion of the bone within the closed path forms a removable portion.

In Example 6, the method of Example 5 can optionally further comprise prying the removable portion away along the closed path to fold over or remove the removable portion; and replacing the removable portion in its original location.

In Example 7 a bone perforator can comprise a bendable sheet having opposing first and second sides; and a plurality of teeth extending from the first side of the sheet, the teeth being spaced along a single-file perforating path; wherein the second side of the sheet is hammerable, so that when the second side of the sheet is hammered against a bone, the plurality of teeth form a perforation in the bone in the shape of the perforating path.

In Example 8, the bone perforator of Example 7 can optionally be configured such that the teeth in the plurality are rigid.

In Example 9, the bone perforator of Examples 7 or 8 can optionally be configured such that each tooth extends away from the first side to a ridge, the ridge being elongated in a direction parallel to the perforating path at the respective tooth.

In Example 10, the bone perforator of one of Examples 7-9 can optionally be configured such that the sheet is configured to be bent cylindrically around an exterior of a femur.

In Example 11, the bone perforator of one of Examples 7-10 can optionally be configured such that the perforating path is L-shaped.

In Example 12, the bone perforator of one of Examples 7-11 can optionally be configured such that the second side of the sheet is flat.

In Example 13, the bone perforator of one of Examples 7-12 can optionally be configured such that away from the perforating path, the sheet has a constant thickness between the first and second sides.

In Example 14, the bone perforator of one of Examples 7-13 can optionally be configured such that the sheet defines at least one hole extending from the first side to the second side.

In Example 15, the bone perforator of one of Examples 7-14 can optionally be configured such that the sheet defines a first pair of holes extending from the first side to the second side at a first longitudinal end of the perforating path; and the sheet defines a second pair of holes extending from the first side to the second side at a second longitudinal end of the perforating path, opposite the first longitudinal end.

In Example 16, a bone perforator can comprise a plurality of segments hinged sequentially to one another along a single-file perforating path; at least some of the segments in the plurality including teeth extending away from the segments; and at least some of the segments in the plurality including a hammerable surface, so that when the hammerable surfaces of the segments are hammered against a bone, the plurality of teeth form a perforation in the bone in the shape of the perforating path.

In Example 17, the bone perforator of Example 16 can optionally be configured such that the segments are hinged parallel to one another and oriented so that the perforating path is repositionable within a plane.

In Example 18, the bone perforator of Example 17 can optionally be configured such that at least some of the segments in the plurality include teeth extending away from the plane on a first side of the plane; and the hammerable surfaces are disposed on a second side, opposite the first side of the plane.

In Example 19, the bone perforator of one of Examples 16-18 can optionally be configured such that the segments are rigid.

In Example 20, the bone perforator of one of Examples 16-18 can optionally be configured such that at least some of the segments are bendable, so that bending at least one of the segments bends the perforating path out of the plane.

In Example 21, the method or bone perforator of any one or any combination of Examples 1-21 can optionally be configured such that all elements, operations, or other options recited are available to use or select from.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the inventors also contemplate examples in which only those elements shown or described are provided. Moreover, the inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, kit, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method for perforating bone, the method comprising:
    positioning a first bone perforator in contact with a bone, the first bone perforator including teeth that extend toward the bone and define a perforating path;
    hammering the first bone perforator, on a side of the first bone perforator opposite the teeth, against the bone along a direction orthogonal to the perforating path, so that the teeth pierce the bone along the perforating path and areas between the teeth do not pierce the bone; and
    removing the first bone perforator from the bone;
    wherein a portion of the bone on one side of the perforating path forms a removable portion; and
    further comprising prying the removable portion away along the perforating path to fold open or remove the removable portion.

2. The method of claim 1, further comprising:
    positioning a second bone perforator in contact with the bone, the second bone perforator including teeth that extend toward the bone and extend the perforating path;
    hammering the second bone perforator, on a side of the second bone perforator opposite the teeth, against the bone, so that the teeth pierce the bone along the extended perforating path and areas between the teeth do not pierce the bone; and
    removing the second bone perforator from the bone.

3. The method of claim 1, further comprising:
    repositioning the teeth on the first bone perforator to form a repositioned configuration for the first bone perforator;
    positioning the first bone perforator in the repositioned configuration in contact with the bone, the first bone perforator in the repositioned configuration including repositioned teeth that extend the perforating path;
    hammering the first bone perforator, on a side of the first bone perforator opposite the teeth, against the bone, so that the teeth pierce the bone along the extended perforating path and areas between the teeth do not pierce the bone; and
    removing the first bone perforator from the bone.

4. The method of claim 1, further comprising:
    alternately:
    repositioning the first bone perforator against the bone to extend the perforating path; and
    hammering the first bone perforator, on a side opposite the teeth, against the bone, so that the teeth pierce the bone along the extended perforating path and areas between the teeth do not pierce the bone.

5. The method of claim 1, further comprising:
    replacing the removable portion in its original location.

6. A bone perforator, comprising:
    a bendable sheet having opposing first and second sides; and
    a plurality of teeth extending from the first side of the sheet, the teeth being spaced along a single-file perforating path;
    wherein the second side of the sheet is hammerable, so that when the second side of the sheet is hammered against a bone, the plurality of teeth form a perforation in the bone in the shape of the perforating path.

7. The bone perforator of claim 6, wherein the teeth in the plurality are rigid.

8. The bone perforator of claim 6, wherein each tooth extends away from the first side to a ridge, the ridge being elongated in a direction parallel to the perforating path at the respective tooth.

9. The bone perforator of claim 6, wherein the sheet is configured to be bent cylindrically around an exterior of a femur.

10. The bone perforator of claim 6, wherein the perforating path includes one of L-shaped, C-shaped, rectangular, zig-zag, or curved.

11. The bone perforator of claim 6, wherein the second side of the sheet is flat.

12. The bone perforator of claim 6, wherein away from the perforating path, the sheet has a constant thickness between the first and second sides.

13. The bone perforator of claim 6, wherein the sheet defines at least one hole extending from the first side to the second side.

14. The bone perforator of claim 6,
    wherein the sheet defines a first pair of holes extending from the first side to the second side at a first longitudinal end of the perforating path; and
    wherein the sheet defines a second pair of holes extending from the first side to the second side at a second longitudinal end of the perforating path, opposite the first longitudinal end.

15. A bone perforator, comprising:
    a plurality of segments hinged sequentially to one another along a single-file perforating path;
    at least some of the segments in the plurality including teeth extending away from the segments; and
    at least some of the segments in the plurality including a hammerable surface, so that when the hammerable surfaces of the segments are hammered against a bone, the plurality of teeth form a perforation in the bone in the shape of the perforating path.

16. The bone perforator of claim 15, wherein the segments are hinged parallel to one another and oriented so that the perforating path is repositionable within a plane.

17. The bone perforator of claim 16,
    wherein at least some of the segments in the plurality include teeth extending away from the plane on a first side of the plane; and
    wherein the hammerable surfaces are disposed on a second side, opposite the first side of the plane.

18. The bone perforator of claim 15, wherein the segments are rigid.

19. The bone perforator of claim 15, wherein at least some of the segments are bendable, so that bending at least one of the segments bends the perforating path out of the plane.

* * * * *